United States Patent
Hudson et al.

(10) Patent No.: US 7,799,048 B2
(45) Date of Patent: *Sep. 21, 2010

(54) NASAL PACKING DEVICE

(75) Inventors: John Overton Hudson, Glenfield (GB); Alberto Bauer, Marbella (ES)

(73) Assignee: ArthroCare Corporation, Austin, TX (US)

( * ) Notice: Subject to any disclaimer, the term of this patent is extended or adjusted under 35 U.S.C. 154(b) by 1140 days.

This patent is subject to a terminal disclaimer.

(21) Appl. No.: 10/258,380

(22) PCT Filed: May 4, 2001

(86) PCT No.: PCT/GB01/01998

§ 371 (c)(1), (2), (4) Date: Oct. 23, 2002

(87) PCT Pub. No.: WO01/85037

PCT Pub. Date: Nov. 15, 2001

(65) Prior Publication Data

US 2003/0236547 A2    Dec. 25, 2003

(51) Int. Cl.
*A61M 29/00* (2006.01)
(52) U.S. Cl. .................................. 606/199; 604/358
(58) Field of Classification Search .............. 606/151, 606/192, 194–196, 199; 604/53, 96.01, 99.01, 604/907, 358; 128/858
See application file for complete search history.

(56) References Cited

U.S. PATENT DOCUMENTS

| | | | |
|---|---|---|---|
| 2,265,387 A | 12/1941 | McMillin | |
| 2,312,679 A | 3/1943 | Speth | 137/234.5 |
| 2,493,326 A | 3/1949 | Trinder | 606/196 |
| 2,847,997 A | 1/1956 | Tibone | 606/196 |
| 3,049,125 A | 3/1960 | Kriwkowitsch | 606/196 |
| 3,420,237 A | 1/1969 | Fortay | 604/96 |
| 3,483,859 A | 12/1969 | Pittman | 600/371 |
| 3,516,407 A * | 6/1970 | Ruggero | 606/196 |
| 3,561,441 A | 2/1971 | Lombardi | 128/156 |
| 3,607,341 A | 9/1971 | Goins et al. | |
| 3,618,607 A | 11/1971 | Ells et al. | 604/368 |
| 3,640,916 A | 2/1972 | Dill | 260/2.5 |
| 3,766,924 A * | 10/1973 | Pidgeon | 606/196 |
| 3,844,947 A | 10/1974 | Sypitkowski | 210/130 |
| 3,919,451 A | 11/1975 | Levy et al. | 428/310 |
| 4,041,948 A | 8/1977 | Flam et al. | 604/369 |

(Continued)

FOREIGN PATENT DOCUMENTS

CA    1150121    7/1983

(Continued)

OTHER PUBLICATIONS

International Search Report from Application No. PCT/GB01/05116, 2002.

(Continued)

*Primary Examiner*—Michael J Milano
*Assistant Examiner*—Victor X Nguyen
(74) *Attorney, Agent, or Firm*—Matthew Scheele; Brian Szymczak

(57) ABSTRACT

A kit for packing and supporting the nasal cavities after surgical procedures performed on the nose comprising two inflatable non-elastomeric balloons (6', 6") and inflation means (27) arranged so that, in use, each balloon (6', 6") can be located in a nasal cavity and inflated.

14 Claims, 8 Drawing Sheets

U.S. PATENT DOCUMENTS

| | | | |
|---|---|---|---|
| 4,044,793 A | 8/1977 | Krueger et al. | |
| 4,241,125 A | 12/1980 | Canning et al. | 428/158 |
| 4,265,965 A | 5/1981 | Chancler | 428/14 |
| 4,326,904 A | 4/1982 | Eckert et al. | 156/85 |
| 4,338,941 A | 7/1982 | Payton | |
| 4,364,392 A | 12/1982 | Strother et al. | 606/195 |
| 4,372,900 A | 2/1983 | Doerfling | 264/45.3 |
| 4,418,524 A | 12/1983 | Ito et al. | 57/239 |
| 4,439,473 A | 3/1984 | Lippman | 428/90 |
| 4,581,017 A | 4/1986 | Sahota | 604/101.01 |
| 4,592,357 A * | 6/1986 | Ersek | 606/199 |
| 4,606,346 A | 8/1986 | Berg | 606/196 |
| 4,619,261 A | 10/1986 | Guerriero | 604/97 |
| 4,638,803 A | 1/1987 | Rand | 606/192 |
| 4,677,016 A | 6/1987 | Ferziger et al. | 428/212 |
| 4,686,962 A | 8/1987 | Haber | 600/30 |
| 4,796,603 A | 1/1989 | Dahlke et al. | 128/899 |
| 4,800,901 A | 1/1989 | Rosenberg | 128/899 |
| 4,832,680 A | 5/1989 | Haber et al. | 600/31 |
| 4,839,222 A | 6/1989 | Jain | 442/375 |
| 4,883,465 A | 11/1989 | Brennan | 604/96 |
| 4,950,280 A | 8/1990 | Brennan | 606/196 |
| 5,011,474 A | 4/1991 | Brennan | 604/540 |
| 5,061,274 A | 10/1991 | Kensey | 606/213 |
| 5,067,497 A * | 11/1991 | Greear et al. | 128/207.15 |
| 5,100,385 A | 3/1992 | Bromander | 604/99 |
| 5,112,678 A | 5/1992 | Gay et al. | 442/173 |
| 5,139,028 A | 8/1992 | Steinhaus | 600/510 |
| 5,139,510 A | 8/1992 | Goldsmith et al. | 606/196 |
| 5,176,692 A | 1/1993 | Wilk et al. | 606/151 |
| 5,224,497 A | 7/1993 | Ehlers | 128/898 |
| 5,263,966 A | 11/1993 | Daneshavar | 606/201 |
| 5,269,296 A | 12/1993 | Landis | |
| 5,308,326 A | 5/1994 | Zimmon | 604/103.1 |
| 5,312,435 A | 5/1994 | Nash et al. | 606/213 |
| 5,327,346 A | 7/1994 | Goodell | 701/71 |
| 5,330,528 A * | 7/1994 | Lazim | 623/1.25 |
| 5,342,298 A | 8/1994 | Michaels et al. | 604/65 |
| 5,376,067 A | 12/1994 | Daneshavar | 602/58 |
| 5,486,195 A * | 1/1996 | Myers et al. | 606/213 |
| 5,514,158 A | 5/1996 | Kanesaka | 606/213 |
| 5,545,176 A | 8/1996 | Murtfeldt | 606/192 |
| 5,571,080 A | 11/1996 | Jensen | 602/56 |
| 5,616,419 A | 4/1997 | Hsu et al. | 428/512 |
| 5,635,248 A | 6/1997 | Hsu et al. | 427/358 |
| 5,643,187 A | 7/1997 | Naestoft et al. | 602/43 |
| 5,645,566 A | 7/1997 | Brenneman et al. | 606/213 |
| 5,731,083 A | 3/1998 | Bahia et al. | 428/393 |
| 5,827,224 A | 10/1998 | Shippert | 604/73 |
| 5,843,060 A | 12/1998 | Cercone | 604/369 |
| 5,906,587 A * | 5/1999 | Zimmon | 604/514 |
| 6,123,697 A | 9/2000 | Shippert | 604/514 |
| 6,191,341 B1 | 2/2001 | Shippert | 604/383 |
| 6,228,068 B1 | 5/2001 | Yoon | 604/246 |
| 6,231,597 B1 | 5/2001 | Deem et al. | 623/1.12 |
| 6,268,544 B1 | 7/2001 | Court et al. | 602/41 |
| 6,274,538 B1 | 8/2001 | Addison | 510/224 |
| 6,306,154 B1 | 10/2001 | Hudson et al. | 606/196 |
| 6,706,051 B2 * | 3/2004 | Hudson et al. | 606/196 |
| 6,746,464 B1 * | 6/2004 | Makower | 606/185 |
| 7,018,392 B2 | 3/2006 | Hudson et al. | 606/192 |
| 7,419,497 B2 | 9/2008 | Muni et al. | 424/434 |
| 2002/0107504 A1 | 8/2002 | Gordon | 604/507 |
| 2005/0043706 A1 | 2/2005 | Eaton et al. | 604/890 |
| 2006/0034930 A1 | 2/2006 | Khosravi et al. | 424/422 |

FOREIGN PATENT DOCUMENTS

| | | |
|---|---|---|
| DE | 3100466 | 9/1982 |
| DE | 4010975 | 10/1991 |
| EP | 0 099 758 | 2/1984 |
| EP | 0 199 531 | 10/1986 |
| EP | 0 252 607 | 5/1987 |
| EP | 0 467 516 | 5/1991 |
| EP | 0 531 096 | 3/1993 |
| EP | 0 864 301 | 9/1998 |
| EP | 0 878 204 | 11/1998 |
| EP | 0 334 913 | 12/1998 |
| GB | 2077111 | 12/1981 |
| GB | 2152384 | 8/1985 |
| GB | 2261819 | 6/1993 |
| JP | 62-97613 | 6/1987 |
| JP | 63-172408 | 9/1988 |
| WO | WO 92/05740 | 4/1992 |
| WO | 93/06855 | 4/1993 |
| WO | WO 93/12275 | 6/1993 |
| WO | WO 93/14724 | 8/1993 |
| WO | WO 93/16658 | 9/1993 |
| WO | 94/06460 | 3/1994 |
| WO | WO 95/19795 | 7/1995 |
| WO | WO 95/20916 | 8/1995 |
| WO | WO 96/39218 | 12/1996 |
| WO | WO 97/39170 | 4/1997 |
| WO | WO 97/22372 | 6/1997 |
| WO | WO 98/09590 | 3/1998 |
| WO | WO 98/57586 | 6/1998 |
| WO | WO 98/46818 | 10/1998 |
| WO | WO9857586 | 12/1998 |
| WO | WO 99/64080 | 12/1999 |
| WO | WO 00/48517 | 8/2000 |
| WO | WO 01/23653 | 9/2000 |
| WO | WO 00/72909 | 12/2000 |
| WO | 01/85037 | 5/2001 |
| WO | 01/85036 | 11/2001 |
| WO | 02/47558 | 6/2002 |

OTHER PUBLICATIONS

PCT International Search Report of International Application No. PCT/GB01/01995, 1995.
PCT International Search Report of International Application No. PCT/GB01/01998, 1999.
"Hi-Lo Tracheal Tube", Mallinckrodt, pp. 1-2, 1998-2001.
"Low Pressure Cuffed Tracheostomy Tubes", Nellcor, pp. 1-2, 2002.
"Tracheal Tubes", Protex, pp. 1-2, 2002.
Journal of Applied Polymer Science, 1973, 17:3375-3389, 1973.
"General Features of an Endotracheal Tube", pp. 1-2, 2001.
UK Patent Office Search Report for Priority Application GB 9712707.0, 1997.
PCT International Search Report for PCT/GB01/01998 7 pgs, Mailed Jul. 16, 2007.
AESCULAP, "Flexible endoscope", Micro, Neuro and Spine surgery, 3 pgs.

* cited by examiner

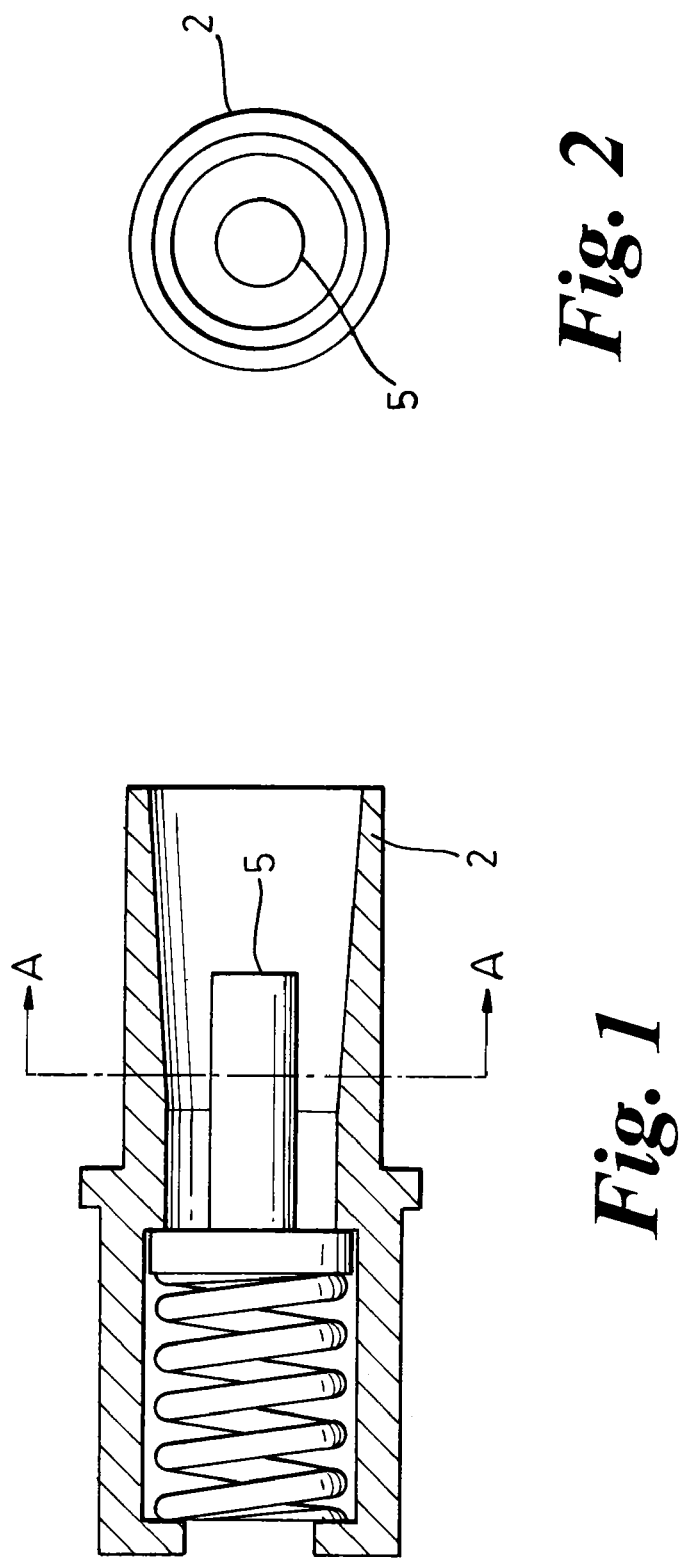

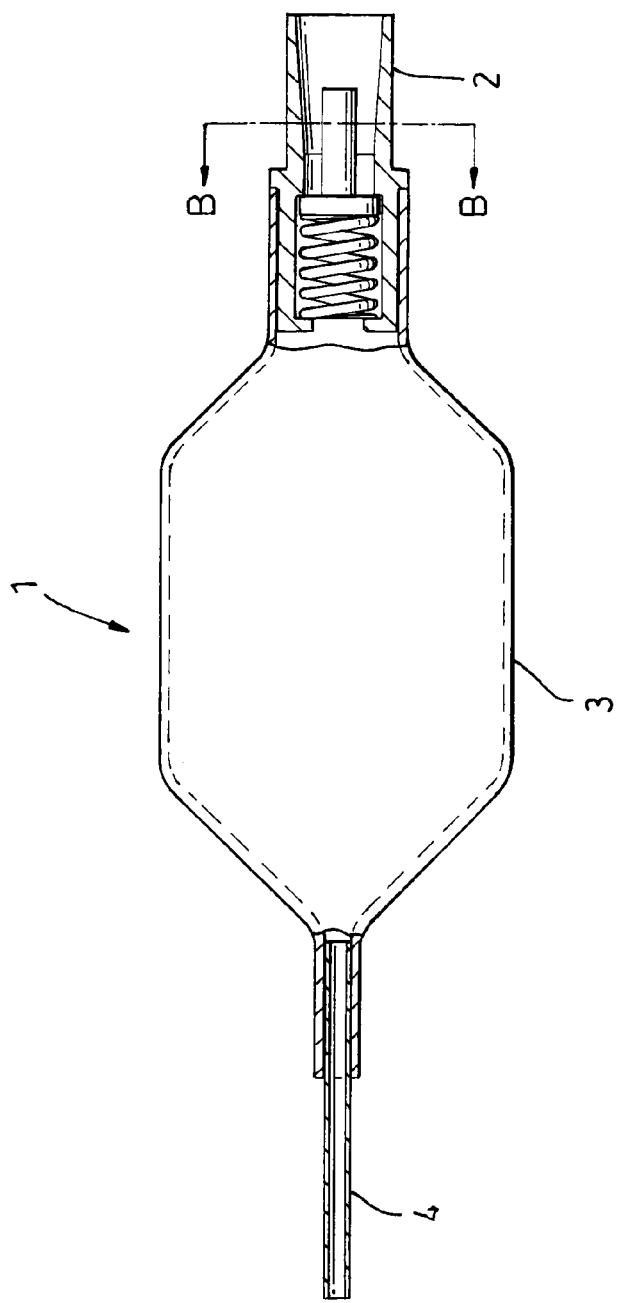

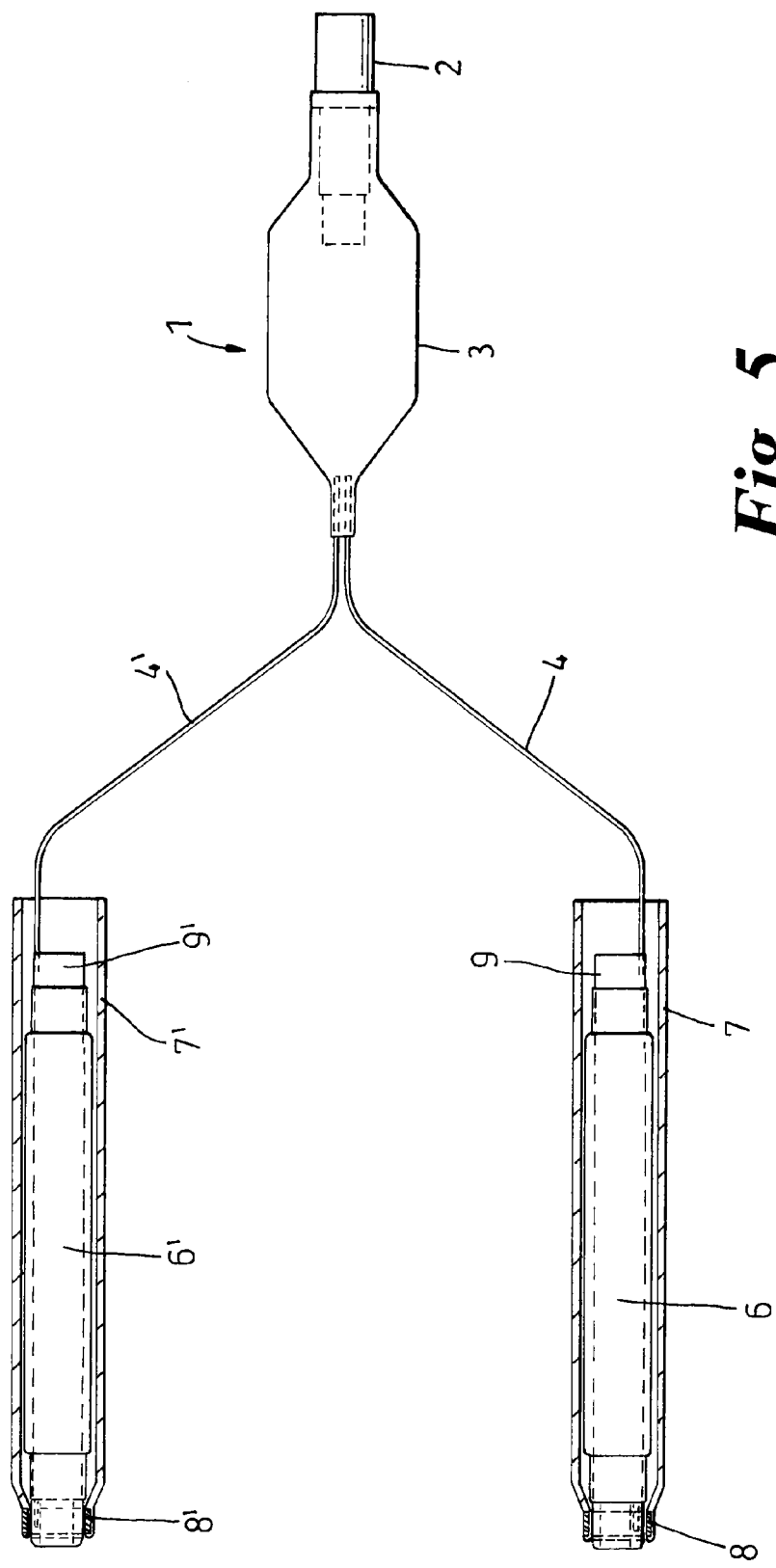

NASAL PACKING DEVICE

CROSS-REFERENCE TO RELATED APPLICATIONS

This application is the U.S. National Stage under 35 U.S.C. 371, of International Patent Application No. PCT/GB01/01998 filed May 4, 2001, which claims priority to U.K. Patent Application No. GB0011053.6 filed May 9, 2000, now abandoned.

BACKGROUND OF THE INVENTION

The present invention relates to apparatus and methods for packing nasal cavities. In particular, the present invention relates to a nasal haemostatic device for packing and supporting the nasal cavities after surgical procedures performed on the nose.

In certain plastic surgical procedures, and in certain plastic surgery (rhinoplasty and septoplasty), it is necessary to cut and modify the nasal septum, that is, the cartilage-like material which separates the left and right chambers of the nose.

There is a technical problem with known nasal packing materials because it is difficult to pack the nasal cavity in a manner that not only ensures good healing but also equal healing on each side of the nasal septum. Moreover, unless great skill is used by the physician, one side of the septum may be packed more tightly than the other side thus causing deformation of the healed septum. Such a deformity is typically regarded as unacceptable by the patient, particularly if the operation was for cosmetic purposes, that is, plastic surgery.

Accordingly, there is a need for improved methods and apparatus for packing nasal cavities.

SUMMARY OF THE PREFERRED EMBODIMENTS

According to a first aspect, the present invention provides a kit for packing nasal cavities comprising two inflatable non-elastomeric balloons and inflation means arranged so that, in use, each balloon can be located in a nasal cavity and inflated.

In use, the balloons are inserted in the left and right chambers of the nose respectively and each balloon inflated. This allows the physician to control the amount of pressure applied to each side of the septum to avoid any possible deformity to the nose.

According to a first embodiment, the inflation means comprises two separate inflation lines, each balloon is connectable to a separate inflation line and each balloon is connectable to a single inflation port by the two separate inflation lines. Preferably, the inflation lines are arranged so that, in use, each balloon is inflated to an identical pressure. This ensures that exactly the same pressure is applied to each side of the septum to avoid any possible deformity to the nose. Moreover, as the method is not reliant on the skill and expertise of a particular physician the apparatus will therefore be more appealing for use by a range of users.

According to a second embodiment, the inflation means comprises a single common inflation line and each balloon is connectable to a single inflation port by the single common inflation line. Preferably, the inflation line is arranged so that, in use, each balloon is inflated to an identical pressure.

The haemostatic nasal packing device according to the second embodiment of the invention allows the user to pack both the anterior and posterior nasal chamber of a single nostril simultaneously following surgical procedures. Moreover, each of the two balloons may be inflated to identical pressures thereby ensuring that exactly the same pressure is applied to the anterior and posterior nasal chamber thus mitigating any possible deformity to the nose.

Preferably, the kit of the present invention includes at least one pressure control means for automatically controlling inflation of the balloons so that each balloon is inflated to an identical predetermined pressure.

According to a third embodiment, the inflation means comprises two separate inflation lines, each balloon is connectable to a separate inflation line and each inflation line includes at least one pressure control means for automatically controlling inflation of the balloon connected thereto so that the balloon is inflated to a predetermined pressure.

The term "automatically controlling the inflation of the balloon so that the balloon is inflated to a predetermined pressure" means that the balloon is inflated to a preselected pressure level without the need for monitoring and/or control by a physician or other users of the device.

The automatic control means solves the technical problem of ensuring that the pressure in the non-elastomeric balloons do not exceed a specific preselected value. This reduces the risk of side effects such as trauma and toxic shock syndrome. Moreover, as the method is not reliant on the skill and expertise of a particular physician the apparatus will therefore be more appealing for use by a range of users. The methods of the invention should result in improved patient compliance compared to alternative surgical procedures.

Still further if separate pressure control means are used and both are preset to different predetermined pressure values then the user may apply different pressures to each side of the nasal septum to induce desirable shape changes during healing.

Preferably, one or both of the balloons has a soft pliable wall made from a non-elastomeric polymeric material.

It is well known to a skilled person in the art that all plastic polymers are elastic to some extent in the strict definition of the word, that is, they obey Hooke's Law and have the ability to return to their original shape after being deformed. However, it is the extent to which the polymers can be deformed which distinguishes non-elastomeric polymeric materials from elastomeric polymeric materials.

By the term "elastomeric polymeric material" we include the meaning of a polymeric material which at room temperature can be stretched to at least twice its original length and upon immediate release of the stress will quickly return to approximately its original length. Examples of elastomeric polymeric materials include rubber and silicon rubber.

By the term "non-elastomeric polymeric material" we include polymeric materials, such as nylon, which, although flexible, do not fall within the functional definition given above for elastomers.

Preferably, one or both of the balloons has a fixed volume which ensures that the pressure in the balloon is independent of the volume of the balloon. The fixed volume non-elastomeric polymeric balloon of the device of the invention ensures that adverse effects associated with wall elasticity of known elastomeric balloons are eliminated or at least substantially mitigated, as all of or most of the pressure within the balloon is directly applied to the wall of the body cavity.

Preferably, the diameter, length and volume of each of the balloons is designed to be slightly greater than that of a nasal cavity likely to be packed during a particular surgical procedure. More preferably, the balloon has a diameter of between 10 mm and 75 mm, a length of between 5 mm and 100 mm and a volume of between 0.5 ml.sup.3 and 450 ml.sup.3.

Preferably, the pressure control means comprises an electrical pressure transducer, well known to a person skilled in the art, which constantly monitors the pressure in the balloons using an electronic instrument. Preferably, the arrangement is directly linked to an electrical inflation device which is programmed to increase the pressure in the balloons to the required predetermined value, and automatically hold it at that value.

Alternatively, the pressure monitoring means comprises a valve that is operable to prevent further inflation of the balloons when the balloons are inflated to the predetermined pressure. More preferably, the valve is a pressure relief valve which is pre-set at the required pressure value and will vent pressure medium when balloon pressure reaches its pre-set value. Most preferably, the valve comprises a tubular member having an outlet in the side wall, a valve cover releasably sealing the outlet and moveable between a sealing position and an open position, and a resilient biasing means, such as a spring, for biasing the valve cover towards the sealing position so that the valve cover moves to the open position when the balloons are inflated above the predetermined pressure. Since the inflation medium is usually air, venting of excess pressure to the atmosphere is most convenient.

Silicone rubber which is used in some elastomeric balloons is permeable to air. Such silicone balloons cannot be inflated with air if inflation is to be sustained. If sustained inflation must be maintained, a silicone balloon must be inflated with a liquid medium such as water or a saline solution.

If air is used as the inflation medium, then non-elastomeric balloons used in the apparatus of the present invention must not be permeable to air. A suitable material is polyvinyl chloride (PVC), but other suitable materials may be used.

Although the relationship between volume and pressure is not linear when using an elastic inflation medium such as air, because the pressure control means is only dependent on the pressure within the balloons this non-linear behaviour of an elastic inflation medium does not affect the operation of the apparatus of the present invention.

By increasing or decreasing the force of the resilient biasing means it is possible to adjust the desirable preset pressure value in the balloons in a quick and cost effective manner. Preferably, the resilient biasing means comprises a spring load pin. The pressure value at which the valve cover will move to the open position thereby allowing the balloons to deflate is dependent on the tension of the spring and the cross-sectional area of the valve opening. Since the valve cover is only held in place by the spring, the apparatus is practically fail safe. Such valves are well known to a person skilled in the art.

In use, a user may use a syringe or a bladder type hand pump which has a larger capacity than that required to inflate the balloon to the predetermined pressure. The syringe is slowly operated to its maximum but the pressure relief valve will vent when the predetermined pressure value is reached. Hence, the balloons are inflated to the required pressure in a simple operation, without any skill or independent pressure control by the user.

Conveniently, a restriction means is provided in the inflation lines distal to the pressure relief valve so that inflation is not carried out too quickly, that is, faster than the venting capacity of the relief valve.

Alternatively, the pressure control means comprises a separate portable pressurised container that is charged with a pressurised inflation medium, such as compressed air. The pressurised inflation medium is charged to a specific value so that when it is connected to the inflation line, the inflatable balloons are charged to a predetermined pressure. It will be apparent to a skilled person in the art that there must be sufficient pressurised inflation medium in the container to counterbalance the pressure drop that will occur by filling the balloons.

In a particular preferred arrangement the pressure control means is operable to permit automatic controlled inflation of, the balloons to at least two predetermined pressures. A particular advantage of such an arrangement is that this allows the balloons to be inflated to a relatively high initial pressure following insertion to attain immediate haemostasis. After this effect has been achieved, typically after 20 to 30 minutes, the pressure in the balloons can be reduced to mitigate possible side-effects such as trauma due to prolonged residence of the balloons in the nasal cavities.

Most preferably, this type of dual pressure inflation arrangement comprises two pressure relief valves, as mentioned hereinbefore, namely a first pressure relief valve that is operable to prevent further inflation of the balloon when the balloons are inflated to the initial predetermined pressure (initially up to 25 KPa); and a second pressure relief valve for reducing the pressure in the inflated balloons to a lower predetermined pressure (between 4 to 12 KPa). This type of arrangement further includes a switching means for independently switching between each of the valves to permit the balloons to be automatically inflated to different predetermined pressures.

Preferably, the switching means is a standard change over valve which may be located either on the input or exhaust side of the pressure relief valves. In use, the change over valve should initially be set so that the high pressure relief valve is in line with the balloons. After the balloon has been inflated, for example with air, for approximately 20 minutes the change over valve can be moved so that the low pressure relief valve is in line with the balloon to allow the balloon to deflate to a lower predetermined pressure.

Alternatively, the dual pressure inflation arrangement may contain a single pressure relief valve which is adapted to permit selective inflation/deflation of the balloons. For example, the tubular member of the pressure relief valve as mentioned hereinbefore may comprise two outlets each of which are releasably sealed by a valve cover. Each valve cover may be biased towards the closed position for example by two separate spring load pin arrangements, as described hereinbefore. Each of the spring loaded pins may have different tensions ie a different spring rate, and/or each of the valve openings/valve covers may have different cross-sectional areas, so that each cover opens at a different predetermined pressure. In this arrangement, the switching means permits selective communication between the balloons, inflation means and independently each outlet of the pressure relief valve.

In both of the dual pressure inflation arrangements including the pressure relief valves, the switching means may comprise removable valve caps sealing the valve outlets. In use, the balloons can be inflated/deflated to the desired predetermined pressure by simply alternately removing and replacing the valve caps.

The device including two separate inflation lines connected to a common inflation port may have a separate pressure control means located in each inflation line or a single common pressure control means located at the proximal end of both inflation lines.

Preferably, the apparatus also includes a delivery means. Preferably, the delivery means for inserting the balloons into the nasal chambers is a catheter which includes the inflation line.

Preferably, the pressure control means is located in the inflation line of the delivery means so that in, use the pressure control means remains outside the patient's body, thereby increasing patient compliance. More preferably, the inflation line includes a restriction distal to the pressure relief valve to ensure that the balloons are not inflated too quickly, in particular so that the balloons are not inflated faster than the venting capacity of the relief valve. This provides the advantage of providing a further additional safety feature to ensure that the balloons are not over inflated.

Preferably, the apparatus includes a non-return valve such as a luer slip valve proximal to the restriction. Preferably, the luer slip valve is opened by the tip of the inflation device ie the syringe to allow the balloons to be inflated and the luer slip valve closes on removal of the inflation device to ensure that the inflated balloons do not deflate completely. It will be appreciated that the inflation device ie the syringe could also be used to deflate an inflated balloon by withdrawing the barrel of the syringe.

Alternatively, the luer slip valve may be operable to permit deflation of an inflated balloon.

Preferably, one or both of the balloons are releasably connected to the delivery means and one or both of the balloons are associated with an agent that retards or prevents bleeding.

The term "an agent that retards or prevents bleeding" includes any haemostatic agent that is capable of arresting, stemming or preventing bleeding by means other than inducing tissue growth alone. In other words, it is not tissue growth alone which is responsible for retarding or preventing bleeding. It will of course be appreciated that the haemostatic agent may have the beneficial property of inducing tissue growth in addition to its retardation or prevention of bleeding property.

Preferably, the haemostatic agent is a bioactive compound or composition which causes vasoconstriction and/or blood coagulation.

Examples of preferred haemostatic agents that retard or prevent bleeding include oxidised cellulose, such as Tabotamp™ sold by Johnson and Johnson, calcium alginate, gelatine or collagen. A particularly preferred agent is carboxymethylated cellulose which can be purchased from Courtaulds Special Fibres, PO Box 111, 101 Lockhurst Lane, Coventry, England, CV6 5RS. Combinations of different agents may be used within the scope of the invention.

Preferably, the haemostatic agent that retards or prevents bleeding is provided in the form of a net or knitted, especially a weft knitted, textile material that envelopes one or both of the balloons. More preferably, the net or knitted textile material is fixed to the balloon(s) and/or has a roughened surface to promote growth of fibrous tissue around the outer surface of the balloon(s) thereby anchoring it to the interior wall of the body cavity.

Alternatively, the haemostatic agent that retards or prevents bleeding is provided in the form of a flexible film that coats the outer surface of the balloon(s). Preferably, the flexible film has a roughened surface to promote tissue growth.

However, it will be appreciated that if the haemostatic agent which prevents or retards bleeding is either in itself or in conjunction with the pressure exerted by the balloons relatively fast-acting, the balloon can be fixed to the delivery means and can simply be pushed inside the nasal cavity until the bleeding has been prevented or retarded and then removed is after the repaired septum has healed.

The invention will be further described with reference to the following non-limiting examples and drawings wherein:

DESCRIPTION OF THE DRAWINGS

FIG. 1 is a side view, partially cross sectioned, of a typical luer slip valve.

FIG. 2 is a plan view of the end of the valve in FIG. 1 taken along the line A-A.

FIG. 3 is the luer slip valve of FIG. 1 incorporated into a safety cuff or pilot balloon.

FIG. 4 is a plan view of the pilot balloon and valve shown in FIG. 3 taken along the line B-B.

FIG. 5 is the first embodiment of the invention with the dual inflatable balloons connected to a single inflation port by separate inflation lines.

DETAILED DESCRIPTION OF THE EMBODIMENTS

1. Standard Inflation Port

Figure 6:
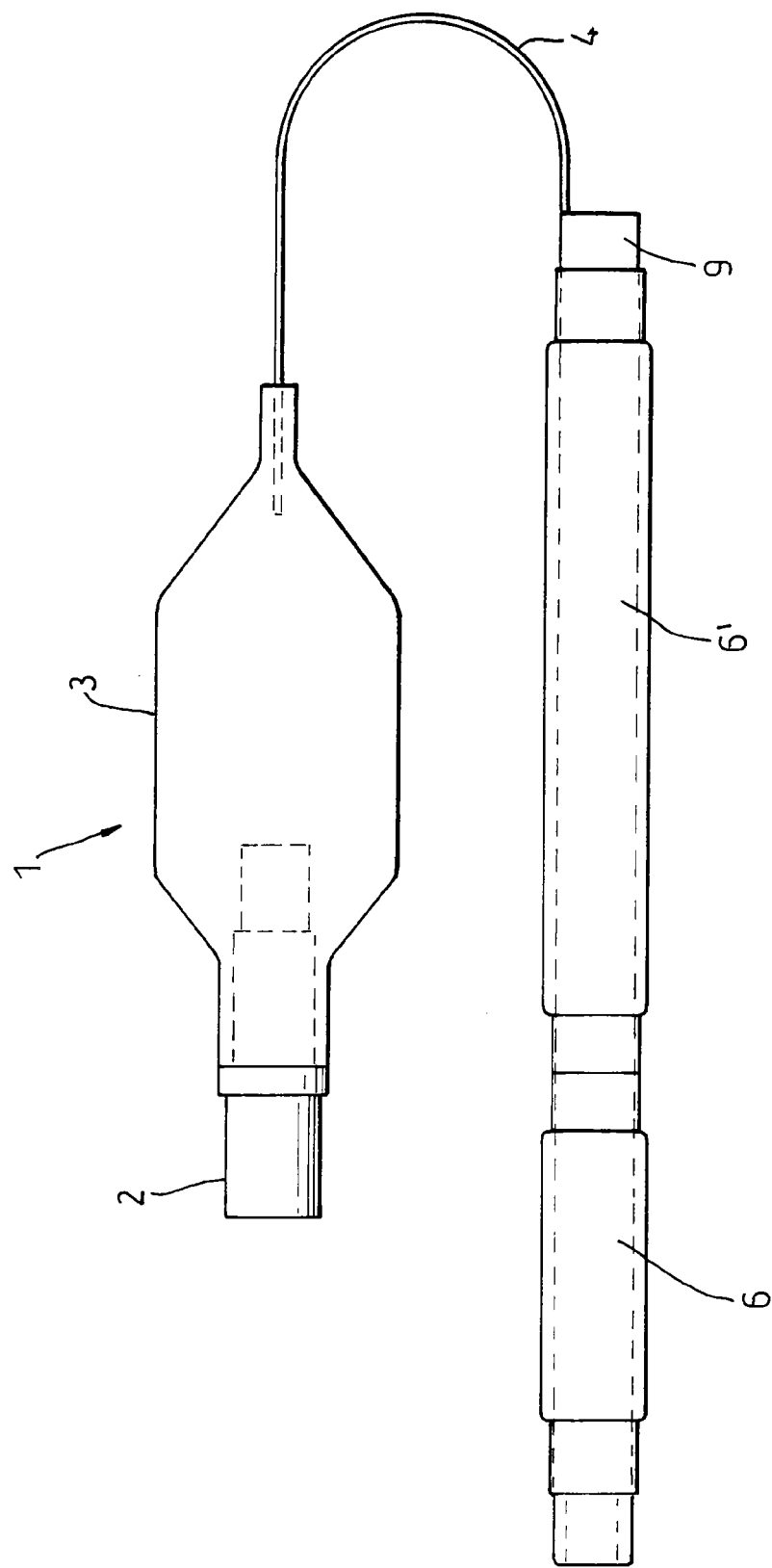
FIG. 6 is another embodiment of the invention with the dual inflatable balloons connected to a single inflation port by a single common inflation line.

There is shown in FIGS. 3 and 4 a typical inflation port arrangement (1) used in a known balloon inflation device suitable for treating a bleeding body cavity. The device (1) consists of a luer slip valve (2), a pilot balloon (3) or safety cuff (3) connectable to an inflation tube (4).

As shown in FIGS. 1 and 2 the luer slip valve (2) includes a port (5) that opens upon insertion of a tip of a syringe and automatically closes when the syringe is removed. Such an arrangement allows a balloon (not shown) to be inflated with an inflation medium and to remain inflated upon removal of the syringe.

It will be appreciated by a person skilled in the art that a bladder type hand pump fitted with a luer type inflation nozzle or a connector which is fitted to a syringe may be used instead of a syringe.

2. Device with Separate Inflation Lines

There is shown in FIG. 5 a haemostatic nasal packing device comprising a typical inflation port arrangement (1) in combination with two inflatable elastomeric balloons (6,6') each of which are in fluid communication with the pilot balloon (3) via separate inflation lines (4,4'). Typically, the inflation lines are about 40-50 mm long.

Each of the balloons (6,6') include a haemostatic fabric shroud (7,7') secured to the distal tip of the respective balloon (6,6') by a fabric ring clamp (8,8'). Each balloon is releasably mounted to a delivery catheter (9,9').

For packing the nasal cavities following a surgical procedure on the nose, the balloons (6,6') and haemostatic fabric shroud (7,7') are inserted into the left and right chambers of the nose respectively. A syringe containing air is inserted into the inflation port (5) of the luer slip valve (2) and air introduced into the apparatus. Both balloons are inflated to identical pressures i.e. between 4 to 25 Kpa.

This enables haemostasis to be achieved and ensures that exactly the same pressure is applied to each side of the septum therefore mitigating any possible deformity to the nose. After the septum has healed the balloons (6,6') are deflated by inserting a syringe into the inflation port (5) of the luer slip valve (2) and withdrawing the barrel of the syringe. The balloons (6,6') are then removed from the nose.

3. Device with a Single Inflation Line

Figure 7:
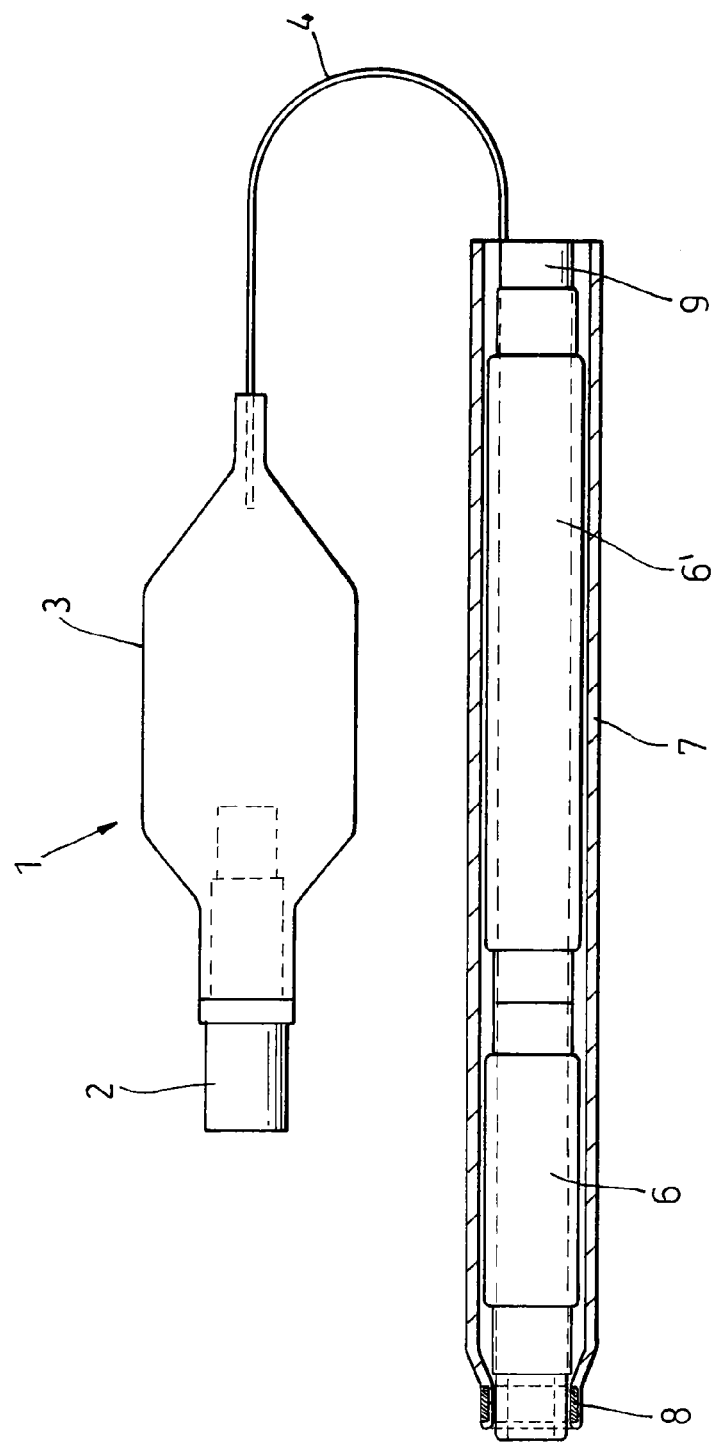
FIG. 7 is the same as FIG. 6 except the balloons include a haemostatic net.

There is shown in FIGS. 6 and 7 a nasal packing device comprising a typical inflation port arrangement (1) in combination with two inflatable elastomeric balloons (6,6') each of which are in fluid communication with the pilot balloon (3) via a single common inflation line (4). Typically, the inflation line is about 40-50 mm long.

The two separate balloons (6,6') are mounted on a common delivery catheter (9) and as illustrated in FIG. 7 the two balloons (6,6') include a haemostatic fabric shroud (7) secured to the distal tip of the distal balloon (6) by a fabric ring clamp (8).

Following a surgical procedure on the nose, the balloons (6,6') are inserted into a single nasal cavity. The balloons of a complimentary device may also be inserted in the other nasal cavity. Inflation and deflation of the balloons may be achieved by following the procedure described hereinbefore (see Section 2 above).

The nasal packing device not only ensures that both balloons (6,6') are inflated to identical pressures but allows the user to pack both the anterior and posterior nasal chambers of a single nostril simultaneously.

4. Pressure Relief Valve

Figure 8:
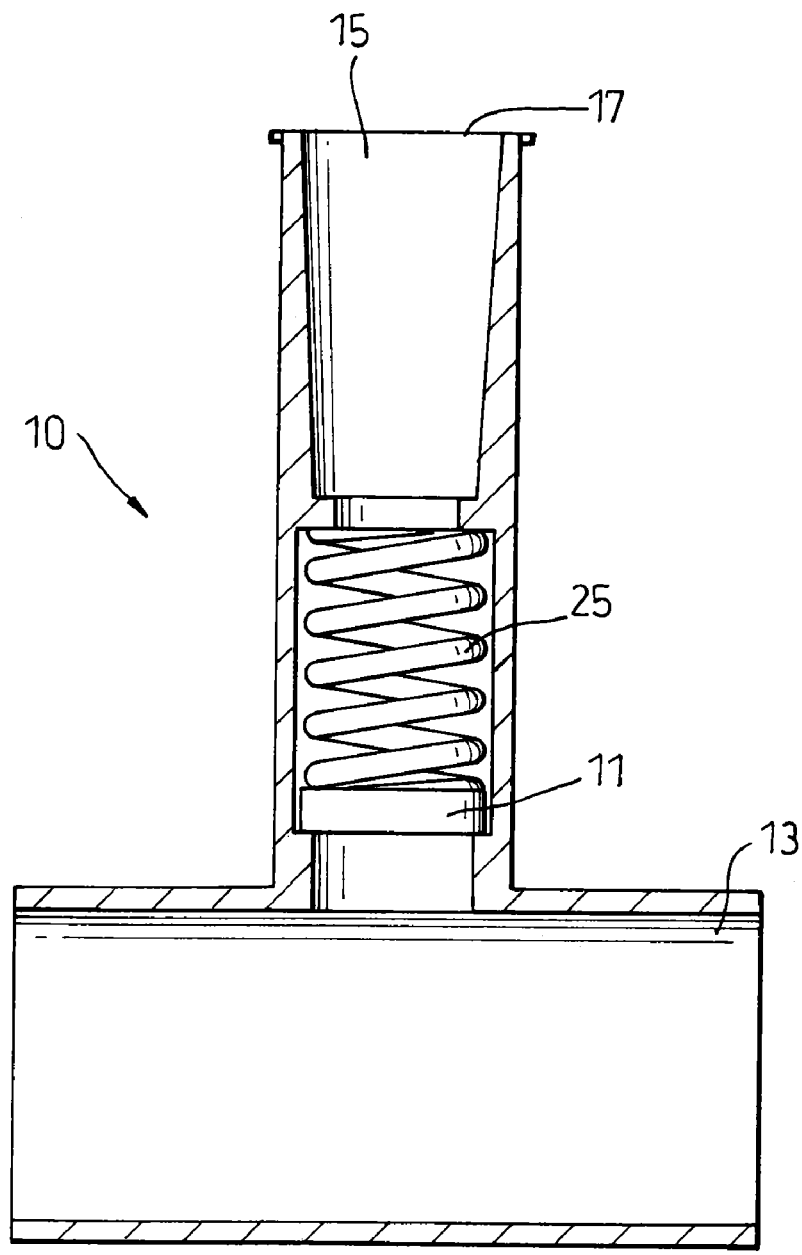
FIG. 8 is a typical pressure relief valve.

A typical pressure relief valve (10) is shown in FIG. 8. The pressure relief valve comprises a spring (25) which biases a sealing gasket (11) in towards a closed position against the pressure generated by the inflation medium in the main chamber (13). When the pressure in the main chamber (13) exerts a force on the sealing gasket (11) which exceeds the force exerted by the spring (25) biasing the sealing gasket (11) towards lo the closed position, the sealing gasket moves to an open position which allows the inflation medium to vent through the release vent (15). When the pressure of the inflation medium in the chamber (13) equals the force of the spring (25) exerted on the sealing gasket (11), the sealing gasket (11) will move from the open to the closed position. Thus the pressure relief valve allows a maximum predetermined pressure to be maintained in the chamber (13). The maximum predetermined pressure may be varied by changing the force exerted by the spring (25) on the sealing gasket (11) and/or by increasing/decreasing the cross-sectional area of the vent/sealing gasket (11).

Preferably, the release vent (15) is in the form of a female luer fitting so that the exit (17) make be sealed with a male luer plug (19).

5. Single Pressure Relief Valve

Figure 9:
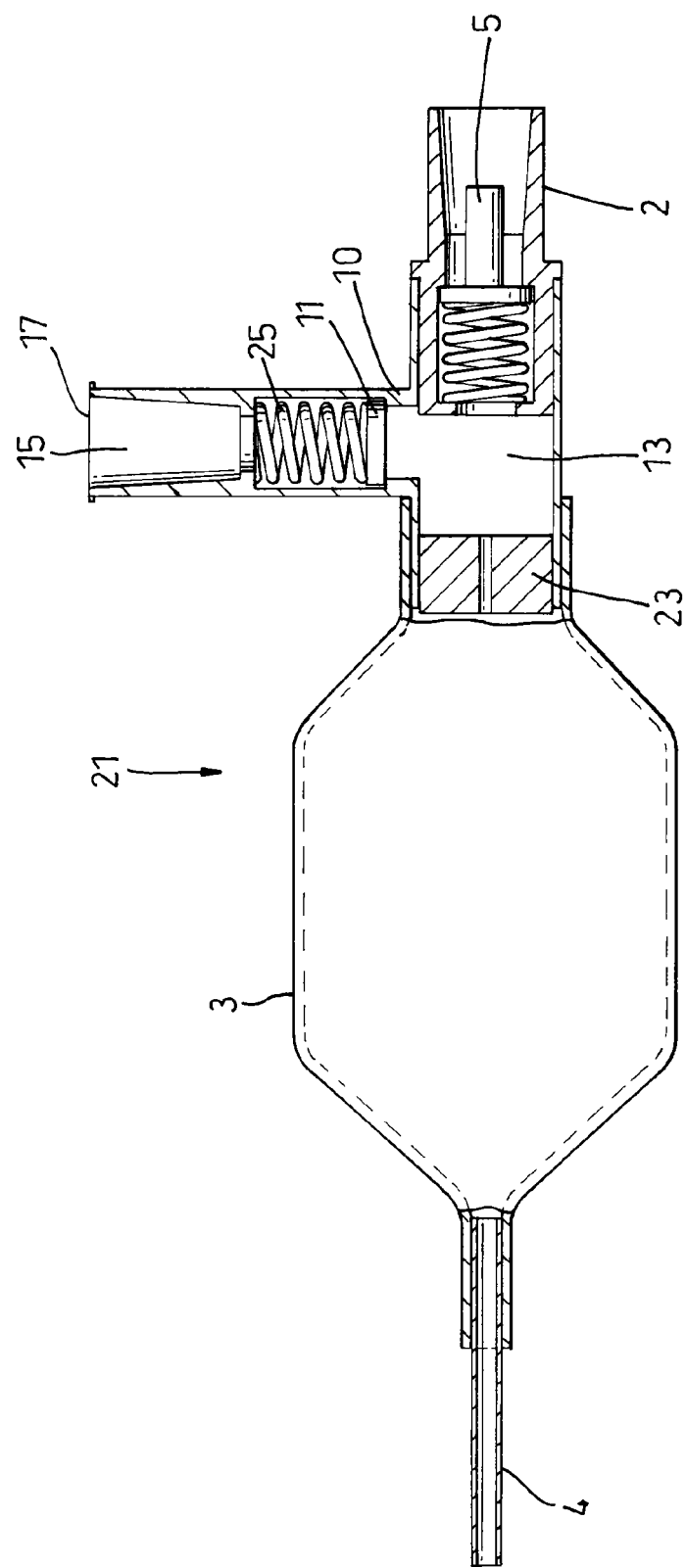
FIG. 9 shows the combination luer slip valve, pressure relief valve, the restriction, the pilot balloon and inflation line.

There is shown in FIG. 9 a preferred embodiment of an inflation port arrangement (21) for use with the apparatus of the present invention comprising a luer slip valve (2), a pressure relief valve (10), a pilot-balloon (3), an inflation line(s) (4) and a restriction (23) distal of the pressure relief valve (10). It will be appreciated that all parts of the inflation port arrangement (21) are in fluid communication with each other and the distal end of the inflation, line(s) (4) is connectable to the non-elastomeric inflatable balloons.

The luer slip valve (2) allows air or another inflation medium to be introduced into the inflation tube (4) via a syringe, thereby inflating the non-elastomeric balloons. The pressure relief valve (10) will allow the inflation medium to vent from the system at a predetermined pressure as described hereinbefore. Hence, this inflation port arrangement (21) allows a user to inflate the balloons to a maximum pre-set pressure and to maintain the inflated balloon at that pressure (ie up to 25 KPa).

The restriction (23) ensures that the pressure of the inflation medium ie air in the inflation tube(s) (4) does not rise above the predetermined maximum value as it prevents the inflation medium from being forced into the inflation tube (4) faster than the rate at which the vent (15) can vent excess pressure in the chamber (13).

6. Dual Pressure Relief Valve

Figure 10:
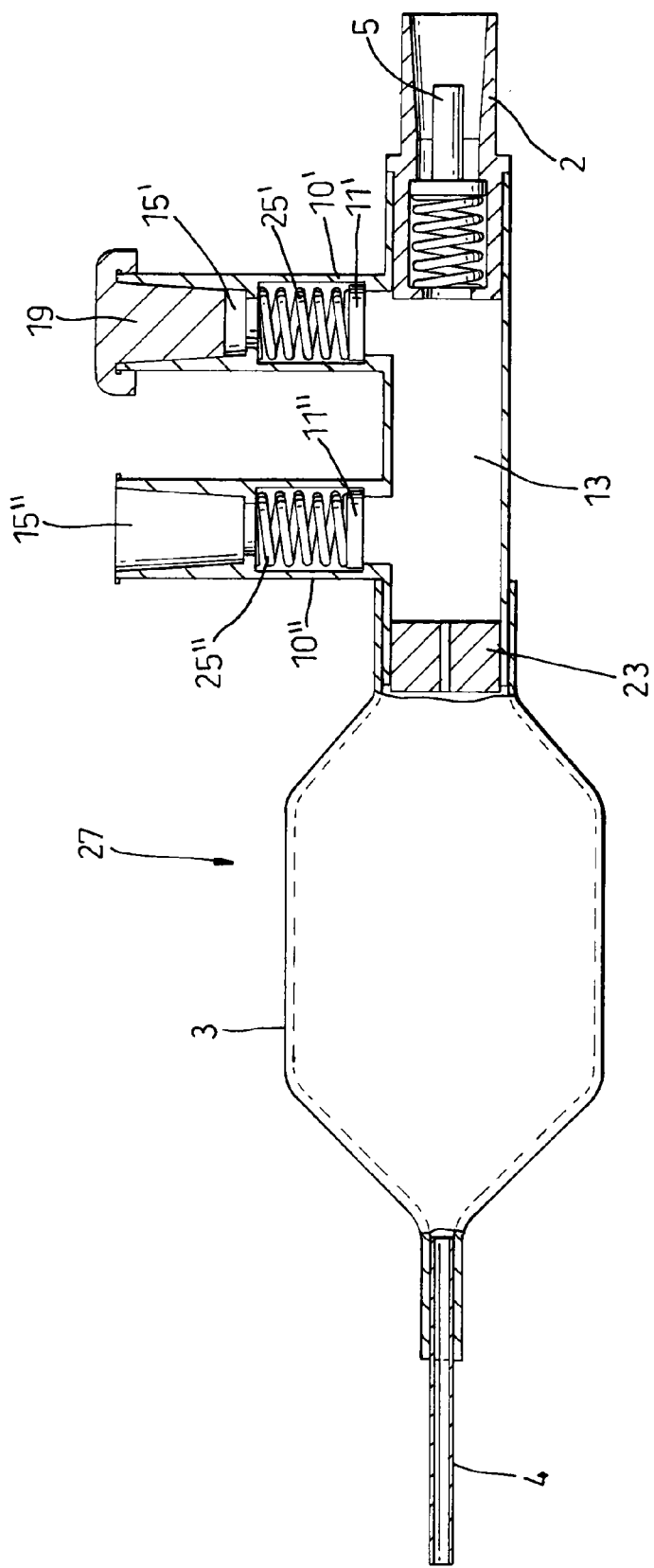
FIG. 10 shows two different pressure relief valves, and a sealing cap on the most proximal, and lowest pressure valve.

There is shown in FIG. 10 an alternative preferred embodiment of an inflation port arrangement (27) for use with the apparatus of the present invention comprising two pressure relief valves (10', 10"), a luer slip valve (2), a pilot balloon (3), an inflation line(s) (4) and a restriction (23) distal of the pressure relief valves (10', 10").

In FIG. 10 and FIG. 11, the parts described herein before are indicated by the same reference numerals.

The two pressure relief valves (10', 10") comprise a pressure relief valve (10') which is adapted to vent at a lower predetermined pressure than the other pressure relief valve (10"). As mentioned above, this may be achieved by using springs (25', 25") having different tensions and sealing gaskets (11', 11") having different cross-sectional areas. This arrangement allows the inflatable balloons (6,6') to be inflated to two different predetermined pressures.

FIG. 11 illustrates the inflation port arrangement (27) in combination with two inflatable non-elastomeric balloons (6',6") mounted on separate delivery catheters (9,9') which are in fluid communication with the inflation lines (4,4').

As described hereinbefore, the balloons (6,6') include a haemostatic fabric shroud (7,7') secured to the distal tip of the balloons (6,6') by a fabric ring clamp (8,8').

Following a surgical procedure, the balloons are inserted into the respective left and right chambers of the nose. The vent (15') of the low pressure relief valve (10') is initially capped with a male luer cap (19) to prevent the inflation medium ie air from venting through this valve (10'). The second higher pressure relief valve (10") initially has its vent (15") open.

A syringe containing air is inserted into the inflation port (5) of the luer slip valve (2) and air introduced into the apparatus. The balloons (6,6') inflate to the higher preset pressure limit, ie between 12 to 25 KPa, as determined by the higher pressure relief valve (10") and remain inflated at this pressure. This high pressure relief valve (10") may be configured so that the pressure in the balloons is slightly higher than normal blood pressure. This enables rapid haemostasis to be attained.

After an initial haemostasis has been achieved the balloon may be deflated to the lower preset pressure, ie between 4 to 12 KPa, by removing the male luer cap (19) from the vent (15') of the low pressure relief valve (10'). This allows the healing nasal cavity to stabilise, it is more comfortable for the patient, and it is less likely to cause medical complications ie deformation of the nasal cavity.

It will be appreciated by a person skilled in the art that although the illustrations in this description have referred to standard luer fittings any suitable seals, fasteners, vents, vent caps and connectors may be used.

Furthermore, any number of pressure relief valves could be used to allow the balloons to be inflated to a number of different pre-set pressure values. Each preset pressure value could be chosen by selectively closing the vents of the pressure relief valves by luer lock caps or some other form of sealing connector.

Alternatively, a valve having a vent sealed with a plug but without a spring loaded seal may be included in the apparatus of the present invention. Removal of the plug from this type of valve will prevent the balloons from being inflated, and if the balloons are already inflated, will cause them to deflate. This type of valve will allow the balloons to be deflated in an emergency situation even if a syringe is not readily to hand.

It is important to match the pressure controlled inflation system with a non-elastomeric, fixed volume balloons. Provided the volume of the balloons are bigger than the nasal chambers which are being treated then the pressure in the system is the same as the pressure applied to the nasal chambers. This is in contrast to using a balloon made from an elastomeric material where some of the pressure in the balloon is utilised in overcoming the forces within the balloon material itself. Consequently, with an elastomeric balloon there is no direct control of the actual force applied to the bleeding cavity.

The devices incorporated in this invention are typically low pressure devices and will work at pressures up to approximately 25 KPa (Kilo pascals). A typical dual pressure device may have the high pressure set between 12 and 25 KPa and the low pressure set between 4 and 12 KPa. However, the principles of the invention should not be restricted to such low pressure devices.

The invention claimed is:

1. A kit for packing nasal cavities comprising two inflatable fixed volume, non-elastomeric balloons arranged so that, in use, each balloon can be located in a nasal cavity and inflated, wherein one or both of the inflatable balloons are coated with an agent that retards or prevents bleeding within the nasal cavity, the agent provided in the form of a net or a knitted textile material that envelopes one or both of the inflatable balloons, wherein the agent further comprises a shroud secured to one or both of the balloons by a fabric ring clamp, and wherein such balloons are arranged such that a left balloon of said balloons may be positioned in the left nasal cavity and a right balloon of said balloons may be positioned in the right nasal cavity, and further comprising two separate inflation lines, each balloon is connectable to a separate inflation line and each balloon is in fluid communication with a single pilot balloon by the two separate inflation lines.

2. A kit as claimed in claim 1 wherein one or both of the balloons are constructed from a non-elastomer polymeric material.

3. A kit as claimed in claim 2 wherein the non-elastomer polymeric material is PVC.

4. A kit as claimed in claim 1 further including a non-return valve to prevent deflation of the balloons.

5. A kit as claimed in claim 4 wherein the non-return valve is a luer slip valve.

6. A kit as claimed in claim 1 wherein one or both of the balloons are not permeable to air.

7. A kit as claimed in claim 1 further including a delivery means.

8. A kit as claimed in claim 7 wherein the delivery means is a catheter.

9. A kit as claimed in claim 7 wherein one or both of the inflatable balloons are releasably connected to the delivery means.

10. A kit as claimed in claim 1 wherein the apparatus is adapted to permit the pressure control means to remain external to the body of a patient.

11. A method of treating a nasal cavity comprising:
inserting both of said balloons of said kit recited in claim 1 into both nasal cavities of a patient such that one balloon is inserted in each nasal cavity;
inflating each of said balloons to a first pressure to pack the nasal cavities; and
after an initial haemostasis has been achieved, reducing the pressure in each of said balloons to a second pressure, the second pressure lower than the first pressure.

12. A kit as claimed in claim 1 wherein the net or knitted textile material has a roughened surface to promote tissue growth.

13. A kit for packing nasal cavities comprising two inflatable fixed volume, non-elastomeric balloons arranged so that, in use, each balloon can be located in a nasal cavity and inflated, wherein one or both of the inflatable balloons are coated with an agent that retards or prevents bleeding within the nasal cavity, the agent provided in the form of a flexible film that coats the outer surface of one or both of the balloons, wherein the agent further comprises a shroud secured to one or both of the balloons by a fabric ring clamp, and wherein such balloons are arranged such that a left balloon of said balloons may be positioned in the left nasal cavity and a right balloon of said balloons may be positioned in the right nasal cavity, and further comprising two separate inflation lines, each balloon is connectable to a separate inflation line and each balloon is in fluid communication with a single pilot balloon by the two separate inflation lines.

14. A kit as claimed in claim 13 wherein the flexible film has a roughened surface to promote tissue growth.

* * * * *